(12) United States Patent
Gorodetsky et al.

(10) Patent No.: US 9,804,121 B2
(45) Date of Patent: Oct. 31, 2017

(54) CEPHALOPOD PROTEINS AS PROTON CONDUCTORS

(71) Applicant: The Regents of the University of California, Oakland, CA (US)

(72) Inventors: Alon Gorodetsky, Irvine, CA (US); Long Phan, Irvine, CA (US); Ward Walkup, Pasadena, CA (US); David Ordinario, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 175 days.

(21) Appl. No.: 14/559,414

(22) Filed: Dec. 3, 2014

(65) Prior Publication Data

US 2016/0377572 A1 Dec. 29, 2016

Related U.S. Application Data

(60) Provisional application No. 61/911,314, filed on Dec. 3, 2013.

(51) Int. Cl.
| | | |
|---|---|---|
| *G01N 27/00* | (2006.01) | |
| *G01N 27/416* | (2006.01) | |
| *C12N 13/00* | (2006.01) | |
| *H01L 51/05* | (2006.01) | |
| *H01L 51/00* | (2006.01) | |

(52) U.S. Cl.
CPC ......... *G01N 27/4167* (2013.01); *C12N 13/00* (2013.01); *H01L 51/0558* (2013.01); *H01L 51/0093* (2013.01)

(58) Field of Classification Search
None
See application file for complete search history.

*Primary Examiner* — Anand Desai
(74) *Attorney, Agent, or Firm* — Mountain IP, pLLC

(57) ABSTRACT

The disclosed invention relates to novel materials and associated methods for conducting protons, such materials comprising cephalopod proton-conducting proteins such as reflectins. The protonic conductivity of such cephalopod proton-conducting proteins may be modulated by the application of an electric field. The invention further encompasses protonic transistors comprising a cephalopod proton-conducting protein channel. The transistors and related devices of the invention are amenable to use in biological systems for the sensing or manipulation of protonic flows within the biological system.

12 Claims, 1 Drawing Sheet

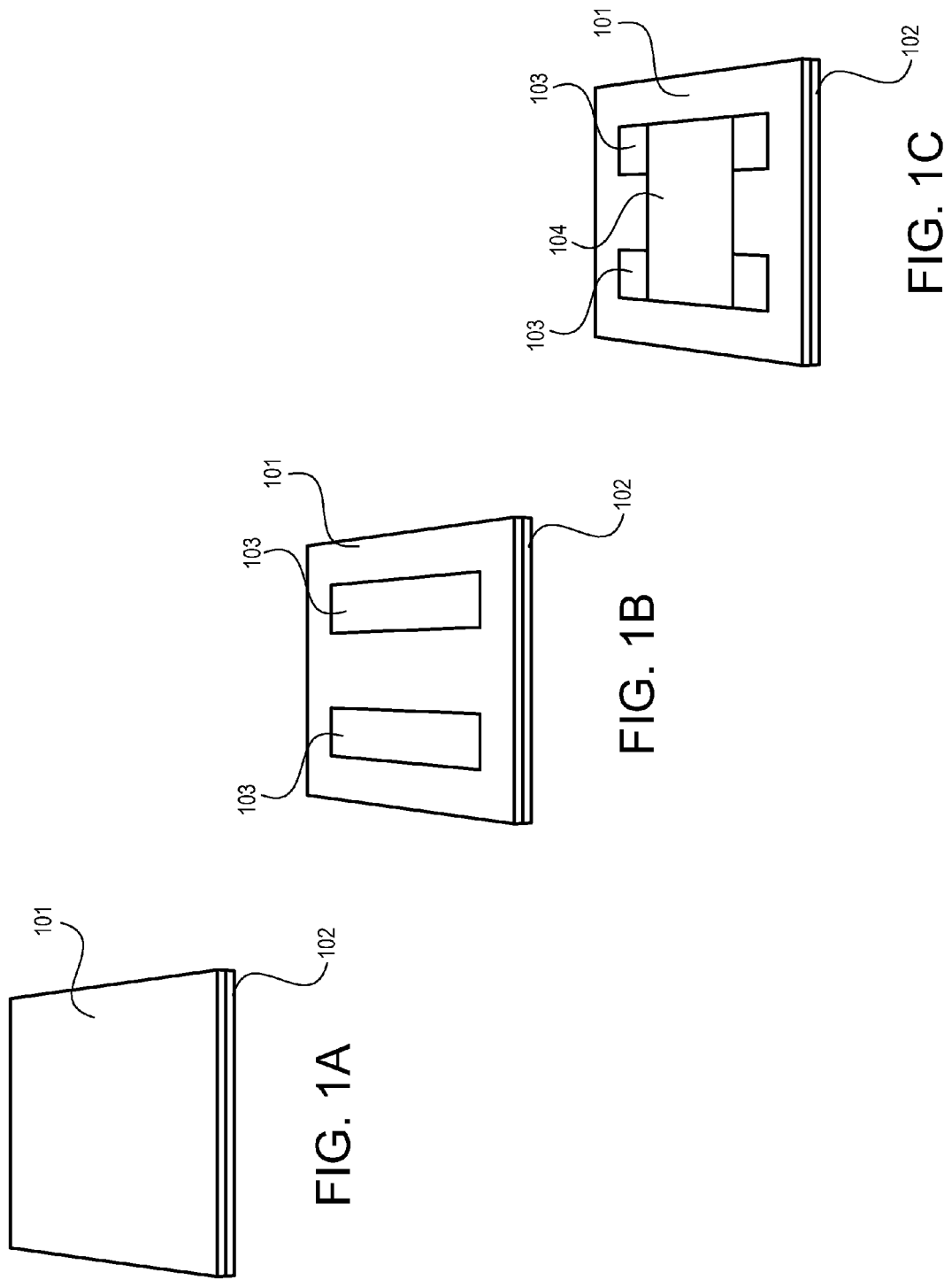

CEPHALOPOD PROTEINS AS PROTON CONDUCTORS

CROSS-REFERENCE TO RELATED APPLICATIONS

This application claims the benefit of priority to U.S. Provisional Application Ser. No. 61/911,314, entitled "Reflectin-Based Transistors and Related Applications," filed Dec. 3, 2013, the contents of which are hereby incorporated by reference.

STATEMENT REGARDING FEDERALLY SPONSORED RESEARCH OR DEVELOPMENT

This invention was made with government support under Grant #FA9550-14-1-0144 awarded by Air Force Office of Scientific Research. The government has certain rights in the invention.

REFERENCE TO SEQUENCE LISTING, A TABLE, OR A COMPUTER PROGRAM LISTING COMPACT DISK APPENDIX

This application is submitted with a computer readable sequence listing, submitted herewith via EFS as the ASCII text file named: "ProtonConductingDomain_ST25.txt", file size approximately 1,349 bytes, created on Dec. 2, 2014 and hereby incorporated by reference in its entirety.

BACKGROUND AND SUMMARY OF THE INVENTION

Proton conduction is one of the most important known natural phenomena. For example, a variety of chemical processes, including redox reactions and acid/base catalysis, are coupled to proton transfer. In addition, numerous biomolecules, such as electrochemically-driven proton pumps in mitochondria and voltage-gated proton channels in phagocytes, have evolved specific structural motifs that facilitate proton translocation. Moreover, the function of an increasingly diverse array of technologically-relevant devices, including fuel cells, electrolyzers, batteries, sensors, and transistors, crucially relies upon proton transport. Indeed, given the ubiquity of proton conduction in chemistry, biology, and materials science, it is hardly surprising that this area has captured the attention of scientists for over two hundred years.

Due to the fundamental and technological importance of proton conduction, solid-state proton-conducting materials, such as ceramic oxides, solid acids, sulfonated polymers, porous solids, and metal-organic frameworks, remain the focus of much research effort. Within this context, naturally occurring proteins have received relatively little attention, which is quite surprising given the prevalence of proton translocation in biology. Moreover, relative to their artificial counterparts, protein-based materials possess notable advantages that include intrinsic biocompatibility, structural modularity, tunable physical properties, ease and specificity of functionalization, and generalized expression/purification protocols. Thus, naturally occurring proteins constitute a promising class of proton conductors, whose potential remains largely unrealized.

From an applications perspective, protein-based proton conducting materials are uniquely positioned to enable the next generation of bioelectronics. For example, given the importance of protons (and ions in general) for electrical signaling in biology, protonic transistors represent a natural choice for interfacing rugged traditional electronics and decidedly more fragile biological systems. Indeed, one can envision the direct and robust transduction of biochemical events into electrical signals with such devices. However, despite this potential for biological applications, there have been very few literature examples of protonic transistors, including a notable recent report of maleic chitosan-based devices from Rolandi and coworkers. Within this context, protonic transistors from naturally occurring materials represent an untapped source of novel materials for various solid-state, bioelectronics, and other devices.

The inventors of the present disclosure have developed a new class of devices based on materials from certain cephalopod structural proteins. Cephalopods are members of the class Cephalopoda and include cuttlefish, squid, and octopus. It has been shown previously that certain proteins from Cephalopods contain a large number of charged amino acid residues, consisting of one to six highly conserved repeating subdomains separated by variable linker regions, and possess little to no secondary/tertiary structure. Some such proteins are also remarkably robust, even when exposed to acidic conditions, heated to 80° C., or processed via standard lithographic protocols. Moreover, within cephalopod skin cells (iridophores), these proteins form platelets, which play a crucial role in cephalopod structural coloration as part of modular Bragg reflector-like structures.

Herein, the inventors of the present invention provide the art with materials derived from such proteins, which such materials have large protonic conductivity and which may be utilized in transistors, proton-permeable membranes, protonic wires, and myriad other structures.

BRIEF DESCRIPTION OF THE FIGURES

FIGS. 1A, 1B, 1C. FIGS. 1A, 1B, and 1C depict the fabrication of a PCCP based transistor. FIG. 1A: A substrate of silicon dioxide (101) is laid down upon a silicon base (102). FIG. 1B: Palladium electrodes (103) are fabricated on the silicon dioxide surface. FIG. 1C: A thin film of PCCP (104) is deposited directly onto the wafer, across the two electrodes. Excess material is mechanically scribed away to create the finished device.

DETAILED DESCRIPTION OF THE INVENTION

The inventors of the present disclosure have discovered that certain proteins may act as proton conductive materials. These proteins will be referred to herein as Proton-Conducting Cephalopod Proteins ("PCCP's"). As set forth below, PCCP's encompass native cephalopod proteins, such as the reflectins, as well as variants of native cephalopod proteins. Furthermore, it will be understood that engineered proteins which include proton-conducting features of native cephalopod proteins will be encompassed within the definition of PCCP's.

The present invention encompasses the use of PCCP's as proton conductors in electronic devices and other applications. Additionally, the inventors have shown that the proton conductivity of PCCP's is responsive to externally-applied electric fields. Accordingly, the invention further encompasses the use of PCCP's in transistors, i.e. devices in which a protonic current flows through a channel comprising PCCP's and wherein the current is increased or decreased by the application of an electric field to such PCCP gate.

Furthermore, the invention encompasses devices for sensing and/or inducing proton fluxes, for example in biological systems.

Proton-Conducting Cephalopod Proteins.

"PCCP's," as used herein, includes polypeptides and proteins which contain one or more proton-conducting domains which enable proton conduction. The proton-conducting domains comprise may comprise three sequential subdomains comprising distinctive sequence motifs: Subdomain 1, Subdomain 2, and Subdomain 3; or may comprise two sequential subdomains: Subdomain 1 and Subdomain 2.

Subdomain 1 comprises a sequence of (M/F)-D-X-X-X-X-X: wherein, in standard one letter amino acid code, M is methionine, F is phenylalanine, and D is aspartic acid, and X is a variable amino acid which may comprise any amino acid. The first amino acid of Subdomain 1, denoted "(M/F)" may comprise either methionine or phenylalanine.

Subdomain 2 comprises a sequence of (M-D-X-X-X-X-X)n: wherein M is methionine and D is aspartic acid, and X is a variable amino acid which may comprise any amino acid. The "n" denotes that this M-D-X-X-X-X-X unit may vary in frequency, for example, n being 0, 1, or 2 in native PCCP's and potentially being greater than 2, e.g. 3-6 in PCCP's comprising engineered variants of native sequences. For clarity, when n=0, Subdomain 2 comprises no amino acids and this sequence motif is not present in the proton-conducting domain.

Subdomain 3 comprises a sequence of M-D-X-X-X or M-D-X-X-X-X, wherein M is methionine and D is aspartic acid, and X is a variable amino acid which may comprise any amino acid.

An exemplary proton-conducting domain sequences is provided in SEQ ID NO: 1. This sequence represents a proton-conducting domain wherein the first amino acid of Subdomain 1 is methionine and may be substituted with phenylalanine; n=2 for subdomain 2, i.e. the motif of Subdomain 2 is repeated two times; and Subdomain 3 is M-D-X-X-X-X, wherein the last amino acid X may be omitted.

Within a PCCP, proton-conducting domains are connected by a linker sequence of variable amino acid composition. The linker sequence may be of any length, for example a linker sequence of 10-60 amino acids, such as a linker sequence of 15-40 amino acids. Preferred linker sequences are those which comprise a flexible chain and which do not form substantial secondary or tertiary structures.

A PCCP may comprise one or more proton conducting domains, for example 1-20 proton-conducting domains. For example, six proton-conducting domains are typically present in reflectins. In engineered versions of PCCP's, any number of proton-conducting domains, for example 1-10 proton-conducting domains, may be present.

It will be understood that substitutions of methionine, phenylalanine, or aspartic acid amino acids in the proton-conducting domains may be present, wherein the substituted amino acid share properties of the substituted methionine, phenylalanine, or aspartic acid, as known in the art, for example as described in Chapter 14 Amino Acid Properties and Consequences of Substitution, Betts and Russell, in Bioinformatics for Geneticists. Edited by Michael R. Barnes and Ian C. Gray Copyright 2003 John Wiley & Sons, Ltd.

In one embodiment, the invention comprises a native PCCP, which is a substantially wild-type form of a protein found in an organism, such as a cephalopod, wherein such protein comprises one or more proton conducting domains. In another embodiment, the invention comprises a variant of a native PCCP, wherein the native sequence has been substituted, truncated, chimerized/fused with one or more non-native sequences, or otherwise altered from the wild type sequence. PCCP's of the invention further include variants, homologs, and modified versions of known native PCCP protein sequences, including chemically or post-translationally modified forms (e.g. phosphorylated, nitrosylated, etc.). For example, native PCCP variants, as used herein, encompass any polypeptide having a detectable degree of sequence similarity, identity or homology to a known native PCCP sequence and having some degree of native PCCP functionality (e.g. proton conductance). This includes sequences having 15-99% sequence identity or similarity (for example 50%, 55%, 60%, 65%, 70%, 75%, 80%, 85%, 90%, 95%, or 99% identity or similarity) to a known native PCCP polypeptide sequence and retaining the proton conductive properties of native PCCP. This also includes sequences of proteins with structural homology to native PCCP, which are defined as proteins with a root mean squared deviation (or equivalent measure of structural similarity) of 5 angstroms or less, as well as when 35 or more main chain atoms amino acids are compared to the native PCCP or its variants, homologs or modified versions. Variants of native PCCP further include polypeptides comprising native PCCP sequences in which one or more amino acids have been substituted, truncated reflectin sequences, and recombinant proteins comprising one or more proton conducting domains.

PCCP protonic conductance may be enabled by the presence of aspartic and glutamic amino acid residues, as well as other charged amino acids such as lysine, arginine, or histidine. Accordingly, in one embodiment, PCCP's include proteins in which non-aspartic and non-glutamic amino acid residues of a native PCCP, for example in the X amino acids of the proton-conducting domain or in the linker sequences, have been substituted with, glutamic acid, and/or other charged residues in order to enhance conductivity. Specifically, PCCP's having increased numbers of aspartic acid, glutamic acid, lysine, arginine, or histidine residues relative to native PCCP's are within the scope of the invention.

In yet another embodiment, the PCCP's comprise engineered sequences, which do not share substantial homology to a native PCCP except for the inclusion of one or more proton-conducting domains spaced by linker sequences.

Native PCCP's include known proteins isolated from cephalopods. An exemplary native PCCP is reflectin. Exemplary reflectin protein sequences include the reflectin A1 protein from *Doryteuthis pealeii* (Also referred to as reflectin-like protein A1; GenBank Accession Number ACZ57764.1) Additional reflectin proteins include the reflectin A2 protein from *Doryteuthis pealeii* (Also referred to as reflectin-like protein A2; GenBank Accession Number ACZ57765.1), and the reflectin B1 protein from *Doryteuthis pealeii* (Also referred to as reflectin-like protein B1; GenBank Accession Number ACZ57766.1). Exemplary reflectin protein further include *Euprymna scolopes* reflectins 1a to 3a; *Sepia officinalis* (SO) reflectins 1 to 11 and x1 to x6; *Loligo pealeaii* reflectins A1, A2, and B1; and a *Loligo forbesi* reflectin rich in menthionines. PCCP's of the invention further include all known isoforms of the reflectin and reflectin-like proteins, as known in the art. Exemplary reflectins include those described in Crookes et al., Reflectins: The Unusual Proteins of Squid Reflective Tissues, Science 303(9):235-238 (2004) and Kramer et al., The self-organizing properties of squid reflectin protein, Nat Mater. 2007 July; 6(7):533-8. (2007). Exemplary reflectin protein sequences further include those described in U.S.

Pat. No. 7,314,735, Identification and characterization of reflectin proteins from squid (Goodson et al.).

The invention further encompasses nucleic acid sequences coding for novel native PCCP variants, and novel engineered PCCP proteins. Nucleic acid sequences coding for such PCCP's include expression vectors, transformation vectors, plasmids, PCR primers, probes, and other nucleic acid sequences known in the art.

As used in the methods and devices of the invention, PCCP's may be derived from any source. For example, PCCP's may be isolated from the squid organisms in which they are found, for example from discarded pen (gladius) as a byproduct of food processing techniques. Preferably, for high yields and inexpensive production, PCCP's may be produced by recombinant protein production methods known in the art. PCCP polypeptide sequences may be produced by any expression system, including bacterial, yeast, insect, and other prokaryotic or eukaryotic cell system, as well as cell-free systems known in the art. For example, PCCP's may be produced in *E. coli* expression systems, for example utilizing His-tagged PCCP fusion proteins.

It will be understood that with respect to the methods and devices of the invention, structures comprising PCCP's are not limited to a single PCCP protein type, and that mixtures of two or more different PCCP's may be utilized.

Functionalization.

Advantageously, as proteins, PCCP's may be readily modified with any number of functional moieties utilizing protein and peptide chemistry conjugation methodologies known in the art. For example, the PCCP's of the invention may be functionalized with materials that: increase their biocompatibility; increase their ability to be tethered or adhered to a substrate or to a biological moiety; decrease their immunogicity; protect them from degradation; and which enhance or supplement the functionalities of the PCCP's. C-terminal, N-terminal, or intraprotein functionalizations or modifications may be made. Such modifications may be performed on PCCP's prior to their incorporation in a structure, such as thin film, or subsequent to such incorporation.

PCCP Materials.

Any material or structure incorporating PCCP's may be utilized in the practice of the invention. As used herein, a "PCCP material" means any material comprising sufficient PCCP's for proton conduction. In one embodiment, PCCP materials of the invention will comprise substantially pure PCCP compositions, such as thin films. In another embodiment, PCCP materials will include composites, wherein PCCP's are incorporated into additional material or materials, as described below.

PCCP Thin Films.

In one embodiment, the PCCP materials of the invention comprise PCCP thin films. PCCP's are readily amenable to the formation of thin films. PCCP thin films may be made by any method known in the art for the creation of protein thin films in general or PCCP thin films in particular, for example as described in Phan et al., Reconfigurable Infrared Camouflage Coatings from a Cephalopod Protein, Adv. Mater. 2013, 25: 5621. Exemplary methods of thin film fabrication include drop casting, spin casting, blading, spraying, printing or any other deposition method known in the art.

For the creation of films, PCCP protein can be essentially purified, such that substantial amounts of contaminants are not present. Alternatively, PCCP's can be used in impure form, i.e. admixed with various constituents. Subsequently, a solution of PCCP is then made. Exemplary solvents include water and hexafluoroisopropanol. This solution is then applied to the substrate, for example by drop casting, spin casting, blading, spraying, printing or any other deposition method known in the art. Subsequently, the film is dried and as the solvent evaporates, a stable thin film of PCCP self-assembles.

In one embodiment, planar PCCP thin films are produced by spin casting or doctor blading. For example, a 500 uM solution of reflectin protein in water may be used, with active heating of the casting surface in order to promote uniform film quality.

In one embodiment, a planar thin film of PCCP is created by the use of doctor-blading. A solution of reflectin protein is prepared, for example 200-1000 uM reflectin, for example 500 uM, in water. The solution is applied to the substrate, and a blade, for example made from polyethylene plastic sheeting, is run over the applied solution to create a smooth layer. Two parallel rails, spaced at the approximate width of the blade, are present on the substrate, and such rails fix the height of the blade above the substrate. The rails may comprise any structure of substantially even height, for example tape, for example Teflon tape having a height of about 150 um. The angle of the blade may be adjusted for optimal application of the protein solution. In general, a lower blade angle results in a thicker film. For example, a blade angle of 45-85 degrees, for example in the range of 60-70 degrees, may be utilized. The speed of the blade can vary, for example in the range of multiple cm per second to multiple cm per minute. For example, a blade speed of 4 cm per minute may be utilized. Exemplary rail heights include those in the range of 20-200 um. Thicker films generally require a higher concentration of protein in the solution, and a more volatile solvent and/or active drying.

For the fabrication of thicker films, multiple layers of PCCP may be deposited on top of one another, for example by multiple cycles of spin casting, drop casting, spraying, printing, dipping, or blading. In this way, films of 300 nm or more may be produced.

Active drying increases the uniformity and quality of the film. Active drying can be any treatment which aids in the rapid evaporation of solvent from the protein solution once it has been applied to the substrate. For example, heating of the substrate from below, or blowing a current of gas over the material behind the blade (for example heated air).

Optionally, an adherent layer may be used to enhance the bonding of the PCCP film to the substrate, for example by covalent, ionic, electrostatic or other forces. In some embodiments, only a single adherent layer is utilized. In such embodiments, the adherent material is capable of both adhering to the substrate and adhering PCCP's. In other embodiments, multiple adherent layers are utilized, each such layer being capable of adhering to the material below it and above it, with the lowermost adherent layer being capable of adhering to the substrate and the uppermost adherent layer being capable of adhering to PCCP's, allowing for the application of PCCP thin films to substrates where direct adhesion with a single layer is not practical due to divergent surface chemistries.

The adherent layer (if a single adherent layer is used) or uppermost adherent layer (if multiple adherent layers are utilized) may comprise any material capable of adhering PCCP's. PCCP's are generally positively charged and hydrophobic. Accordingly, preferred materials for such layer are those having negative charge and/or hydrophobicity. Hydrophobic materials may be entirely hydrophobic or may be amphipathic, having partial hydrophobic properties. An exemplary material for the adherent layer is graphene oxide.

Graphene oxide is negatively charged and amphipathic and will stably and strongly bind PCCP's. Graphene oxide is also readily deposited on substrates such as silicon and glass and other materials. Advantageously, graphene oxide is inexpensive and water soluble, making it easy to utilize in manufacturing. Another exemplary class of materials for the adherent layer is the alkanethiol compounds, which readily form self-assembled monolayers on a number of surfaces. The head group of the alkanethiol can be selected for effective bonding to the substrate, and the tail group is capable of modification (e.g. to impart negative charge and/or hydrophobicity) such that it can effectively bind or adhere to PCCP's.

PCCP Composites.

In one embodiment, the PCCP material of the invention comprises any materials wherein PCCP's combined with or incorporated into one or more secondary materials. The function of the secondary materials will generally be to provide a substrate or support for PCCP's, such that the resulting composite can be molded, milled, deposited, or otherwise formed into a desired structure. The secondary materials may provide other functions, for example protection of PCCP's from degradation. The density of PCCP particulate material within the composite material may vary, however, in general, a sufficiently dense network of interconnected PCCP's to enable efficient bulk proton transfer will be desired. In another embodiment, the PCCP material will comprise a secondary material having a plurality of PCCP vias or wires traversing the channel structure.

In one embodiment, the invention encompasses a composite material comprising PCCP'-coated particulate carriers in a polymeric matrix. For example, PCCP's may be deposited onto, adsorbed onto, absorbed by, or encapsulated within a particulate body, such as a sphere (e.g. a microsphere or nanosphere), such particulate body being composed of any material, for example a polymeric material, metallic, or ceramic material. These carrier particles may further be incorporated into a polymeric material, carbohydrate matrix, lipid matrix, or other material. Exemplary polymeric materials include PDMS, PMMA, PEDOT:PSS, and PEG, as well as any derivatives thereof.

PCCP Structures.

PCCP materials such as thin film and composites may be incorporated in or fabricated into any number of structures and devices, including microscale and nanoscale structures. In some embodiments, the PCCP structure comprises a substrate. Exemplary substrates include metallic materials, glass, silicon and silicon-containing materials, ceramics, metals, polymeric materials, and natural materials. Depending on the intended use, proton-insulating, or proton donating substrate materials may be used. Exemplary substrates structures include wafers, beads, particles, mesh or porous supporting structures, fibers, tubes, etc. The invention further contemplates the use of PCCP's in combination with other proton-conducting materials, such as ceramic oxides, solid acids, sulfonated polymers, porous solids, and metal-organic hybrids.

Water Content.

The protonic conductivity of PCCP's is, generally, highly dependent upon the degree of water saturation of PCCP materials. More hydrated PCCP structures, presumably having more free protons to donate to current flows, are observed to have higher protonic conductivity than films with less water saturation. In many embodiments, it is contemplated that the PCCP materials and structures of the invention will be wholly or substantially immersed in solutions or will be present in a highly hydrated environment such as a biological environment (e.g. intracellular spaces, extracellular spaces, or cell culture media). When PCCP materials are to be utilized as proton conductors in a non-immersed environment, maintaining water content to enhance proton conductance may be accomplished by any methods that ensure adequate water intercalation into PCCP structures. For example, maintaining PCCP elements in an aqueous environment, or an environment with at least 50% humidity, for example 80-99% humidity, will promote fuller saturation of the material and increase the protonic conductivity of such materials. For example PCCP components may be sealed in substantially watertight vessels or encasements with adequate water or water vapor present to maintain high humidity around such PCCP components. Alternatively, external sources of water vapor may be used to humidify the vicinity of the PCCP components.

In one embodiment, the hydration status of the PCCP component is used to controllably change the protonic conductivity of the component. Increasing the hydration status of the PCCP material will increase protonic conductivity while reducing hydration will inhibit protonic conductivity within the PCCP material or structure.

Applications of PCCP Materials.

PCCP Wires or Channels.

In a basic implementation of the invention, the invention comprises a PCCP-containing material or structure which acts as a protonic wire, for conducting protonic currents or flows from a proton source to a proton sink. Such articles of manufacture comprise protonic channel structures, or "channels." It will understood that "channel," as used herein means a conduit for the flow of protons and does not imply a physical channel (e.g. ditch or groove) structure. For example, the PCCP-containing structure acting as a wire or channel for the flow of protons may be included in an electronic device.

The invention further encompasses a method of conducting protons from a proton source to a proton sink though a PCCP material or structure. A proton source and proton sink may comprise any material, structure, spatial area, or volume of liquid, wherein protons flow from the source to the sink. For example, the source and sink may comprise elements of a protonic circuit, wherein a potential difference between the source and sink drives proton movements through a PCCP channel. In another example, the source an sink may comprise discreet areas having different proton concentrations, wherein the proton concentration gradient drives proton movement through or across the PCCP channel.

PCCP Membranes.

In another embodiment, the invention comprises a PCCP membrane. The membrane may comprise a PCCP material which is deposited onto or within a porous or perforated support, such as a mesh. The PCCP membranes of the invention may be used in any number of contexts, for example in electrochemical cells, electrolyzers, fuel cells, bio-hydrogen reactors, or any other context where selective movement of protons from a first compartment to second compartment is desired, a "compartment" comprising any discreet or continuous space, including a vessel, lumen, an intracellular space, an extracellular space, or a bulk solution. In a related embodiment, the invention further comprises a method of selectively allowing the movement of protons from a first compartment to a second compartment by the use of a PCCP membrane separating the two compartments.

PCCP Coatings.

In another embodiment, the invention comprises a coating of PCCP material applied to a structure. For example, in one embodiment, the invention comprises an electrode, catalyst, or electrocatalytic element coated with a PCCP material, for example an electrode, catalyst, or electrocatalytic element in a fuel cell, battery, electrolyzer, etc. For example, such coatings may be used to allow selective transport of protons to and from electrodes while increasing the biocompatibility of the electrode, inhibiting the fouling of the electrode, etc.

Electrical Control of PCCP Proton Conductivity.

The inventors of the present disclosure have advantageously discovered that PCCP conductivity is responsive to applied electric fields. Exposure of a PCCP material to a negatively charged electric field will inhibit the flow of protons though the PCCP material. Exposure of a PCCP material to a positive electric field will increase the conductivity of protons through the PCCP material. When applying fields to PCCP films, such as reflectin thin films having thickness of 0.1 to 500 microns, electric field strength may be in the range of $10^2$-$10^7$ V/m to effectively control conductivity of the material. In one embodiment, the invention comprises a method of controlling the conductivity of a PCCP material by the application of an electric field to the PCCP material, wherein the application of a negatively charged electric field decreases the conductivity of the PCCP material and the application of a positively charged electric field increases the conductivity of the PCCP material.

PCCP Transistors.

Accordingly, PCCP materials may be utilized in protonic field-effect transistors, with the PCCP materials acting as protonic semiconductors. In one embodiment, the invention comprises a PCCP transistor, comprising a source electrode, a drain electrode, a PCCP channel, and a gate electrode which can apply positive or negative electric fields to the PCCP channel.

The protonic field effect transistors of the invention may be implemented in various forms, for example, as FET switches and FET amplifiers. Other device types include depletion FET's, enhancement FET's, and induced FET's.

The transistor devices of the invention comprise a source electrode and a drain electrode. The electrodes may comprise any conductive material, for example gold, silver, copper, aluminum, and conductive metallic and/or organometallic alloys. Metallic materials which are amenable to standard device electrode deposition techniques may be used, for example metallic materials deposited by electroplating or other deposition methods. Especially preferred are electrodes which can emit or absorb protons, promoting proton current flow. For example, electrodes from metal hydrides or any other materials that conduct protons, including ceramic oxides, solid acids, sulfonated polymers, porous solids, and metal-organic frameworks, may be used. For example, palladium-hydride (PdHx) electrodes, as known in the art, may be utilized. Other hydride electrode materials include $LixMn2O4$, Pt-PdHx alloys, PtHx, NiHx, or any metal hydride known in the art. Noble metals, being inert, are particularly useful materials for hydride electrodes.

The protonic transistors of the invention further comprise a channel comprising PCCP material. The PCCP material will have a sufficient concentration of interconnected PCCP's such that protons may efficiently pass through the material. An exemplary PCCP material is a thin film of PCCP's, for example a reflectin thin film. Channel geometry and structure may vary, as described below.

(001) The channel will be in contact with or in proximity to a gate electrode. The gate electrode is any structure which can apply an electric field to the PCCP channel, such electric field being of sufficient strength to affect the conductivity of the PCCP channel. Gate electrodes for the field effect transistors of the invention include any gate electrode configuration known in the art. Any conductive material typically utilized to create a gate electrode in solid state devices may be used, and, likewise, any known dielectric, such as silicon dioxide, may be utilized as the dielectric material separating the electrode from the PCCP channel, such that a voltage applied to the gate electrode exerts an electric field on the PCCP channel.

The protonic transistors of the invention may comprise any number of configurations. For example, in one embodiment, the invention comprises a planar protonic transistor, for example as depicted in FIG. 1 and in Examples 1 and 2. The planar transistor comprises a planar substrate of insulating or non-proton conducting dielectric material, for example silicon or silicon dioxide or any other oxides commonly used in semiconductor fabrication, such as hafnium-based dielectrics. For example, a single crystal silicon wafer with an approximately 3000 Angstrom thick silicon dioxide layer may be used as the substrate.

Source and drain electrodes may then be fabricated onto the substrate by any means known in the art, for example deposition, printing, etc., the source and drain electrodes separated by a distance, for example a distance of 10-5000 nanometers. Source and drain electrodes may comprise any material, preferably a material capable of emitting or absorbing protons, such as metal hydride electrodes, e.g. PdHx electrodes. In one embodiment, a PCCP material, for example a reflectin thin film, is deposited directly onto the dielectric substrate and the electrodes, for example as described in Examples 1 and 2. In another embodiment, the PCCP channel is fabricated on a separate substrate, cut to the desired dimensions, and is placed, PCCP side-down, onto the substrate and across the electrodes.

A gate electrode is placed in contact with or in close proximity to the PCCP channel. The gate electrode may be fabricated upon a previously placed or deposited PCCP channel, or may be fabricated separately and then positioned on or near the PCCP channel. In one embodiment, the PCCP channel is integral to a gate electrode assembly, the channel comprising a PCCP thin film, for example a reflectin thin film, fabricated on a dielectric substrate, with a conducting electrode being disposed on the opposite side of the dielectric substrate.

The configuration of channel, source and drain electrodes, and gate electrodes may vary. For example, the transistor of the invention may comprise a network of metal hydride electrodes overlaid by or embedded within a PCCP channel material. Likewise, a plurality of gate electrodes may be overlaid on or embedded within a PCCP channel structure. Planar transistors are amendable to large scale processing techniques, such as lithographic and deposition methods. Other transistor geometries are within the scope of the invention, and may be useful for specific applications, such as micro-scale and nano-scale probes, for example filamentous probes.

As known in the art, channel geometry in a transistor or like device is an important aspect of device performance characteristics. Channel length, channel width, active layer thickness, and oxide thickness are important factors to consider in optimizing the properties of a transistor or like device. In general, rules applicable to transistor design for semiconductors will be applicable to the design of PCCP based devices. For example, as described in Example 2, channel thickness significantly affects the performance of a PCCP device. Specifically, PCCP films, such as reflectin thin films of 0.20-0.50 microns in thickness, for example films of 0.30 microns in thickness, will have significantly improved current high/low ratios, compared to thicker PCCP films, for example 1-2 microns in thickness.

PCCP Proton Emitters/Absorbers.

In one embodiment, the invention comprises a device for controllably emitting or withdrawing protons from the local environment of the device. In a proton emitter, the device comprises a proton source. The proton source may be a proton electrode, i.e. an electrode capable of emitting or absorbing protons based on an applied voltage. For example, a metal hydride electrode such as PdHx may comprise the proton source. The proton source may alternately be a proton donating material, such as an acidic solution. The proton source is isolated from its surrounding environment by an encasing structure, the encasing structure comprising a PCCP channel, such as a membrane, protonic wire, or other channel configuration. The PCCP structure is also in contact with or in proximity to a gating electrode which may apply sufficient electric field to the PCCP structure to increase or decrease the protonic conductivity of the PCCP structure. When the electric field is altered such that protonic conductivity is increased, protons are increasingly able to travel from the proton source, through the PCCP channel, to the surrounding environment. When the electric field is altered such that protonic conductivity is decreased, the flow of protons from the protonic source is decreased or substantially halted. Accordingly, the invention further encompasses a related method of controllably emitting protons to the surrounding environment of a proton source by increasing or decreasing the protonic conductivity of a PCCP channel disposed between the proton source and surrounding environment, by means of an applied electric field.

Similarly, the device of the invention may comprise a proton absorber, i.e. a device capable of withdrawing protons from the surrounding environment. The proton absorber comprises a proton sink, i.e. a structure or material capable of absorbing protons. For example, in one embodiment, the proton sink may comprise a metal hydride electrode to which a negative potential is applied. In another embodiment, the proton sink may comprise a material or solution which absorbs, traps, or sequesters protons, for example a basic material or a material such as cardiolipin. The proton sink is isolated from its surrounding environment in an encasement structure comprising a PCCP channel. The PCCP channel is also in contact with or in proximity to a gating electrode, such that an electric field may be controllably applied to the PCCP channel in order to increase or decrease its protonic conductivity, allowing an increased or decreased rate of proton travel from the surrounding environment to the proton sink through the PCCP channel, resulting in withdrawal of protons from the surrounding environment. Accordingly, the invention further encompasses a related method of controllably withdrawing protons from the environment surrounding a proton sink by applying an electric field to a PCCP channel disposed between the proton sink and the surrounding environment, by means of an applied electric field.

PCCP Sensors.

In another embodiment, the invention comprises a sensor for measuring proton concentration or fluxes in a target environment. In one embodiment, the invention comprises a PCCP channel disposed between two electrodes, for example, two metal hydride electrodes. A protonic current is generated by applying potential difference between the two electrodes. The PCCP channel is in contact with the surrounding environment. When the proton concentration, i.e. pH, of the surrounding environment changes, the concentration of protons in the PCCP channel is increased or decreased, the current between the two electrodes will be altered proportionally. For example, an increase in the local proton concentration will increase the conductivity of the PCCP channel and a decrease in the local proton concentration will decrease the PCCP channel's protonic conductivity. Such changes in conductivity may be measured by changes in current flow between the source and drain electrode. The sensing device of the invention may further comprise a gating electrode to tune the conductivity of the PCCP channel for maximum sensitivity in the given environment. The invention further encompasses a related method of sensing changes in local proton concentrations by observing changes in protonic current through a PCCP channel, the PCCP channel being in contact with the surrounding environment and connecting a source and drain electrode.

Other Applications.

PCCP's may be utilized in materials wherever proton conduction is required. For example, applications wherein selective conduction of protons, but not electrical currents is desired. In one aspect, PCCP's may be utilized as protonic wires. In other applications, PCCP materials may be utilized in the same manner as Nafion™ or similar materials, for example in metal-ion recovery, water electrolysis, plating, surface treatment of metals, batteries, biosensors, Donnan dialysis cells, drug release, gas drying or humidification, and acid catalysis for the production of fine chemicals.

Biological Applications.

The protonic transistors and other devices of the invention may be utilized in various biological applications. Specifically, the PCCP devices and methods of the invention may be applied in biological systems for sensing of protonic fluxes in a biological system (i.e. monitoring biological functions) or for the injection or withdrawal of protons in a biological system (i.e. perturbing or controlling biological functions). As a protein based material, PCCP materials are more highly amenable to use in biological environments than traditional electronic materials, and PCCP structures may act as an interface between biological systems and electronic components. Furthermore, PCCP materials are readily fabricated in micrometer and nanometer sizes, allowing their use at biologically relevant scales.

The use of PCCP devices is contemplated for any biological system. For example, such devices and methods may be applied in vivo, ex vivo (e.g. to explants) or cell culture. The method and devices of the invention may be applied in any cell or organism type, for example in eukaryotic, prokaryotic, human, mammalian, yeast, or bacterial systems.

In one embodiment, PCCP materials and devices such as proton emitters/absorbers or sensors may be used in intracellular implants or probes in living cells, for example in filamentous configurations such as nanowires. Likewise, PCCP materials and devices may be utilized at the tissue or organ level, being implanted or inserted into extracellular spaces or within tissues or cultured cells. Additionally, PCCP materials or devices may be utilized as substrates for cell culture. Given the high lysine/arginine content of native PCCP's such as reflectin, such proteins may serve as effective substrates for cell growth in the same manner that poly-lysine serves as an adhesion layer for directed cell attachment. Additionally, PCCP materials are amenable to well developed methods of protein modification, and, for example may incorporate binding moieties capable of binding complementary binding moieties (e.g. biotin-avidin, integrins, selectins, and cadherins) for the purpose of tethering or immobilizing cells, vesicles, or other biological components to the PCCP device or surface.

(002) In one embodiment, PCCP sensors are used to measure proton fluxes in biological systems, for example in response to developmental events or external stimuli, e.g. the administration of active agents such as agonists or inhibitors of a specific process. In another embodiment, PCCP devices are used to controllably inject protons or withdraw protons from a system for the purpose of manipulating specific biological processes, e.g. for research or therapeutic purposes.

EXAMPLES

Example 1

Herein is described the characterization of the conductive properties of platelet-like thin films from a *Loligo (Doryteuthis) pealeii* reflectin A1 isoform (See references 44-46).

Materials and Methods: (I) Design and Cloning of Wild Type Mutant Reflectin A1 Genes: A. Wild Type Reflectin A1:

An *E. coli* codon optimized gene coding for 6× Histidine-tagged wild type reflectin A1 protein from *Loligo (Doryteuthis) pealeii* (Genbank: ACZ57764.1) was synthesized and cloned into pJExpress414 vector (DNA 2.0). Mutant: The DE→A mutant reflectin A1 protein was designed using Gene Designer 2.0 software (DNA2.0). To generate the DE→A mutant reflectin A1, all aspartic acid (GAT/GAC) and glutamic acid (GAA/GAG) codons in wild type reflectin A1 were replaced with alanine codons (GCA/GCC/GCG/GCT), resulting in a total of 34 DE→A mutations. The DE→A reflectin A1 mutant gene was then synthesized (GeneArt) and restriction cloned into a pJExpress414 plasmid in frame with an N-terminal 6× Histidine Tag. The DE→A sequence is shown in FIG. S11. C. Random Mutant: A scrambled mutant reflectin A1 protein was designed using the Emboss shuffleseq and Needle algorithms. The wild type reflectin A1 sequence was input into Emboss shuffleseq and run for 20 shufflings. The resulting sequences were then force aligned in pairwise alignments with wild type reflectin A1 using the Emboss Needle algorithm (BLOSUM62 matrix, 100 Gap Open, 10 Gap Extend, End Gap Penalty True, 10 End Gap Open, 10 End Gap Extend), and the resulting alignments were examined to select a Randomized reflectin A1 protein sequence that lacked any (M/F-D-X5)(M-DX5)n(M-D-X3-4) repeats and exhibited minimal global pairwise sequence identity (7.4%) to wild type reflectin A1. The scrambled sequence is shown in Ordinario et al. (2014).

(II) Expression and Purification of Wild Type and Mutant Reflectin A1:

A general protocol was used for the expression and purification of wild type, DE→A, and Random mutant reflectin A1. In brief, the pJExpress414 expression vectors containing wild type or mutant reflectin were transformed into BL21(DE3) cells (Novagen). Reflectins were expressed at 37° C. using Overnight Express Instant Terrific Broth (TB) media (Novagen) supplemented with 100 g/mL Carbenicillin. Reflectin was completely insoluble when expressed at 37° C. and was sequestered in inclusion bodies prepared using Novagen BugBuster™ according to the manufacturer's suggested protocol. Reflectin inclusion bodies were then solubilized in denaturing buffer (pH 7.4, 50 mM Sodium Phosphate, 300 mM NaCl, 6M guanidine hydrochloride) and purified under denaturing conditions on HisPur Cobalt Resin (Thermo Scientific) immobilized metal affinity chromatography (IMAC) gravity columns according to the manufacturer's protocols. The protein was eluted by using denaturing buffer supplemented with 250 mM imidazole. The fractions containing reflectin were pooled and concentrated on Millipore Amicon Concentrators before being purified with high performance liquid chromatography (HPLC) on an Agilent 1260 Infinity system using an Agilent reverse phase C18 column with a gradient evolved from 95% Buffer A:5% Buffer B to 5% Buffer A:95% Buffer B at a flow rate of 0.5 mL/min over 20 minutes (Buffer A: 99.9% H2O, 0.1% TFA; Buffer B: 95% acetonitrile, 4.9% H2O, 0.1% TFA). The pure reflectin fractions were pooled, flash frozen in liquid nitrogen, and lyophilized. Protein concentrations and yields were quantified via a Bradford protein assay with bovine serum albumin (BSA) as a standard (BioRad).

(III) Purification, Analysis, and Sequence Confirmation of Reflectin A1:

A general protocol was used for the purification, analysis, and sequence confirmation of both wild type and mutant reflectin A1. In brief, Sodium Dodecyl Sulfate Polyacrylamide Gel Electrophoresis (SDS-PAGE) and GelCode Blue staining were performed to assay protein purity and analyze reflectin yields throughout the purification process. Thus, purified and unpurified reflectin samples were analyzed by SDS-PAGE and GelCode Blue Staining (Thermo) using an Invitrogen XCell SureLock Mini using NuPAGE Novex 4-12% Bis-Tris gels, with NuPAGE MOPS as the running buffer under reducing conditions. Stained protein bands were subjected to in-gel tryptic digestion, performed according to literature procedures (66). After digestion, the peptides were separated on a C18 chromatography column and analyzed by mass spectrometry on a Thermo Orbitrap instrument outfitted with an electrospray ionization source. The resulting sequence coverage was 94% for wild type reflectin A1, 94% for the DE→A mutant reflectin A1 and 34% for the Random mutant reflectin A1.

(IV) Fabrication of Reflectin Devices: A. Preparation of Substrates:

The substrates were fabricated from 4" silicon wafers grown by the Czochralski method. The p-type Boron doped wafers were 405 to 455 thick with a <100> crystallographic orientation and 3000 Å oxide layer on both sides (International Wafer Service, Inc.). The wafers were sectioned into individual 1.5 cm² Si—SiO2 chips using standard lithographic techniques. Prior to deposition of electrodes, the substrates were cleaned in piranha solution (1:3 hydrogen peroxide to sulfuric acid).

B. Device Fabrication:

The electrodes consisted of a 4 nm chromium layer overlaid with a 40 nm gold or palladium layer. The metals were deposited onto the surfaces of each substrate via shadow mask lithography with a BJD 1800 Electron Beam Deposition System (Temescal). To fabricate completed devices, reflectin films were drop cast onto the electrodes and air dried overnight. The coatings were mechanically scribed to leave a rectangular reflectin film between each electrode pair. Reflectin films fabricated in this fashion were smooth and featureless, as determined by AFM (V) Electrical Characterization of Reflectin Devices: A. Two-Terminal Measurements with Gold or Palladium Electrodes:

Current as a function of voltage was recorded in a humidified environment on a PM-5 Probe Station (Cascade Microtech) outfitted with a 4156C Semiconductor Parameter Analyzer (Agilent). The electrical measurements were performed under ambient conditions at different relative humidities. The dimensions of each electrode were 100 m by 400 m with an inter-electrode separation of 50 m.

B. Three-Terminal Measurements with Palladium Hydride Electrodes:

Current was recorded as a function of source-drain voltage (at different gate voltages) in a humidified environment on a PM-5 Probe Station (Cascade Microtech) outfitted with a 4156C Semiconductor Parameter Analyzer (Agilent). The electrical measurements were performed under a 5% hydrogen/95% argon atmosphere. The dimensions of each electrode were 100 m by 400 m with a channel length of 50 m.

Electrochemical Impedance Spectroscopy Measurements with Gold Electrodes:

Impedance data was recorded with a Hewlett Packard 4192A LF Impedance Analyzer or an Agilent 4294A Impedance Analyzer. The electrical measurements were performed in a humidified environment at various frequencies with a constant applied voltage of 500 mV. Data was collected at temperatures between 25° C. to 65° C. Before each measurement, a 30 minute dwell at each temperature was used to ensure thermal stability. The dimensions of each electrode were 2.5 cm by 3 cm with an inter-electrode separation of 100 m.

(VI) Electrochemistry of Reflectin Thin Films A. Preparation of Reflectin-Modified Electrodes:

Electrochemical experiments were performed with gold working electrodes with a diameter of 2 mm (CH Instruments, Inc.). The electrodes were sequentially polished with 0.05 m and 0.3 m wet alumina slurries on microcloth (Buehler, Inc.). The electrodes were then thoroughly rinsed and sonicated in Milli-Q water to remove remaining adsorbed alumina traces. The electrodes were subsequently electrochemically etched in 1 M H2SO4 to expose a clean gold surface and rinsed again with Milli-Q water. Reflectin A1 was deposited directly onto the clean electrode and a film of the protein was allowed to dry in air overnight.

B. Cyclic Voltammetry of Reflectin Thin Films:

Cyclic voltammetry (CV) experiments were performed in a three-electrode electrochemical cell on a CH Instruments CHI832C Electrochemical Analyzer. The reflectin-modified gold electrode served as the working electrode, a platinum wire served as the counter electrode, and a silver/silver chloride electrode served as the reference electrode. The measurements were performed in pH=7.2, 1 M phosphate, 1.5 M sodium chloride 10×PBS buffer, which was purged with argon (Thermo Scientific, Inc.). The high salt content buffer was selected to ensure that the reflectin film remained bound to the electrode during the electrochemical measurements.

(VII) Microscopy of Reflectin Thin Films

A. Optical Microscopy:

Each reflectin film was imaged with an Axio Imager AIM (Zeiss) outfitted with an Epiplan 20X, NA=0.4 lens (Zeiss). The image data was processed with AxioVision AC Release 4.5 (Zeiss).

B. Atomic Force Microscopy:

The thickness of all reflectin films was measured with atomic force microscopy (AFM) by examining trenches scribed directly into the films. The AFM data was processed with the Gwyddion software package. Topological scans were rastered at 0.17 Hz and normalized using polynomial subtraction for improved image quality. Thickness scans were rastered at 1.0 Hz to ensure a complete trace over the surface under different humidity conditions. The films were examined in situ with a MFP-3D AFM (Asylum Research) outfitted with a Humidity Sensing Cell (Asylum Research).

(VIII) Water Uptake of Reflectin and Reflectin Mutants A. Preparation of Reflectin Samples:

A small amount of either wild type reflectin, the DE→A mutant, or the Random mutant was weighed out onto a clean platinum pan (typical amount of ~1 to ~5 mg). The sample was then hydrated in either water or deuterated oxide vapor at a relative humidity of 90% immediately prior to analysis.

B. Analysis of Reflectin Samples:

Thermogravimetric analysis of mass loss due to solvent uptake was performed on a TGA Q500 instrument (TA Instruments, Inc.). Sample pans containing either wild type reflectin or the mutants were loaded into the instrument and heated under a nitrogen atmosphere at a ramp rate of 20° C. per minute, from room temperature to 350° C.

(IX) Details of Calculations:

Calculations were performed as described in Ordinario et al., Bulk protonic conductivity in a Cephalopod structural protein, *Nature Chemistry* 6. 596-602 (2014).

Results.

A histidine-tagged *Loligo* (*Doryteuthis*) *pealeii* reflectin A1 isoform was heterologously expressed in *E. coli*. Reflectin A1 dinclusion bodies were first prepared according to standard protocols (46). The protein was then sequentially purified via immobilized metal affinity chromatography (IMAC) under denaturing conditions and high performance liquid chromatography (HPLC) (46). The identity of the purified reflectin was definitively confirmed by in-gel tryptic digestion and mass spectrometry (46). The protocol yielded >800 mg pure protein per liter of cell culture, facilitating the throughput of subsequent electrical experiments (See reference 46).

For the electrical measurements, two- and three-terminal bottom contact devices were fabricated, where reflectin served as the active material. In brief, shadow mask lithography was used to electron-beam evaporate arrays of paired gold (or palladium) electrodes onto either silicon/silicon dioxide (Si/SiO2) or glass substrates. Subsequently, smooth and featureless thin films of reflectin were drop cast directly onto these electrodes from aqueous solution and excess material was carefully mechanically scribed away, taking great care to avoid damaging the electrodes. The completed devices were then subjected to systematic electrical interrogation.

The electrical properties of reflectin in a two-terminal configuration were investigated by recording current as a function of voltage, with gold electrodes serving as the electrical contacts on $Si/SiO_2$. To avoid contributions from water electrolysis, applied potentials were limited to below ~1.5 V, which is the thermoneutral voltage for this reaction; typically, electrolysis requires even larger biases due to the presence of an overpotential (See references 50, 51). Here, completely dry reflectin films at relative humidities of <50% revealed current levels on the order of a few picoamps, which were similar to the current levels found in the absence of bridging material. However, at high relative humidities (90%), reflectin films exhibited a marked increase in the current density to 0.6 (±0.2) A/cm2 at 1.5 V across a set of 16 films. The resulting current versus voltage characteristics displayed a clear deviation from linearity and significant hysteresis between the forward and reverse scans; this behavior qualitatively resembled that found for maleic chitosan proton conductors contacted by blocking gold electrodes (See reference 40). Such non-ideal characteristics indicated the presence of capacitive effects and/or carrier blocking at the electrical contacts, consistent with protonic (and ionic) conduction (See reference 52).

It was sought to gain insight into whether reflectin's conductivity was protonic (See references 6, 10, 36) or electronic (See references 36, 53-55) in origin (both types of mechanisms are well known for proteins). Electronic conduction in proteins requires holes or electrons to hop or tunnel between peptides or cofactors that are readily oxidized or reduced (See references 53-55). Thus, the electrochemical properties of reflectin were investigated in a standard three-electrode configuration with cyclic voltammetry. Results revealed that reflectin was electrochemically silent over a potential window of ~1.5 V on gold, with no distinct oxidation or reduction peaks. The lack of electrochemical activity suggested that electronic conduction was unlikely for reflectin.

To better understand the mechanism of conduction for reflectin, electrochemical impedance spectroscopy (EIS) was used to interrogate reflectin-based devices contacted with gold electrodes on glass substrates. Alternating current (AC) potentials were applied to the films and plotted the real and imaginary parts of the impedance in Nyquist plots (See references 56, 57). The plots displayed a semicircle in the high frequency region and an inclined spur in the low frequency region. Curves of this kind are a fingerprint of protonic conductors contacted by gold electrodes, where the semicircle corresponds to a bulk protonic impedance and the spur corresponds to the pile up of protons at the blocking electrodes (See references 56-60). Thus, the curves were fit with a simple equivalent circuit, which has been shown to accurately model proton exchange membranes by accounting for the bulk impedance and capacitive effects at the contacts (See references 56-60). The high quality of the fit indicated that this simple model was applicable for the reflectin films, and the equivalent circuit yielded a bulk resistance, which translated to an effective conductivity of $1.0 (\pm 0.5) \times 10^{-4}$ S/cm across a set of 9 films. Overall, the EIS measurements indicated that proton conduction was likely for this material.

As additional evidence for protonic conduction in reflectin films, observation of the kinetic isotope effect was sought for the two-terminal reflectin-based devices. To this end, EIS measurements were recorded for reflectin films contacted with gold electrodes on glass in the presence of deuterated oxide ($D_2O$). At identical relative humidities, the solvent uptake of deuterated oxide was almost identical to that of water for reflectin films, ensuring a reliable comparison. Here, a distinct isotope effect was observed, in close agreement with literature observations for other proton-conducting materials (See references 11-16); upon going from $H_2O$ to $D_2O$, the Nyquist plots showed identical characteristic inclined spurs, but the conductivity changed by 40% from $1.0 (\pm 0.5) \times 10^{-4}$ S/cm to $0.6 (\pm 0.3) \times 10^{-4}$ S/cm across a set of 9 films. This measurement supported the notion of bulk protonic conduction in reflectin films.

Subsequently, the electrical properties of reflectin were interrogated when contacted with proton-transparent palladium hydride (PdHx) electrodes. PdHx facilitates proton injection without electrolysis, yielding higher currents for proton-conducting materials (and lower currents for electron-conducting materials) (See references 40, 61). Therefore two-terminal devices were fabricated with Pd as the electrode material these devices were exposed to H2 gas, facilitating the formation of PdHx electrical contacts in situ (See references 40,61). Electrical measurements for these devices yielded a current density of $8.2 (\pm 5.9)$ A/cm2 at 1.5 V and a relative humidity of 90% across a set of 16 films, which were over an order of magnitude higher than those found for gold electrodes. Hysteresis consistent with charge accumulation/depletion at the contacts were recorded (See reference 40); relative to devices with gold electrodes, the hysteresis was somewhat reduced, presumably due to improved charge injection. Thus, the observations were fully consistent with the notion of proton conduction in reflectin films.

The properties of reflectin films contacted with PdHx electrodes at different levels of hydration was also explored. Previous studies have demonstrated that reflectin effectively behaves as a hydrogel, swelling as a function of relative humidity (See references 43,44,46). Here, reflectin devices displayed a noticeable increase in the current level with humidity. For biomolecular proton conductors, water uptake induces the formation of hydrogen-bonded proton conduction pathways, facilitating Grotthuss-type proton transfer (See references 10,18-20, 40). Given the large number of charged/hydrophilic residues found in reflectin (See references 43, 44, 46) the same effect likely accounts for the observed increase in current with relative humidity. Notably, for electronic conductors, even low levels of moisture should lead to lower current levels (the opposite effect) due to the likelihood of irreversible reactions (formation of defects and traps). Overall, the observations with PdHx contacts could only be rationalized by assuming a proton conduction mechanism for reflectin.

To gain insight into the structural origins of reflectin's conductive properties, reflectin's advantages as a protein-based material were leveraged and targeted mutations were introduced within its primary sequence. At neutral pH, the excess protons necessary for conductivity in hydrated reflectin likely originate from deprotonation of the carboxylic acids on its aspartic (D) and glutamic (E) amino acid residues (pKa's of 3.9 and 4.3, respectively); lysine, arginine, and histidine are expected to make a relatively small contribution to the number of free protons (See reference 62). Thus, eliminating the carboxylic acid-containing residues in reflectin should effectively shut off a protonic conductor but have little effect on an electronic conductor. To test this hypothesis, a reflectin mutant was heterologously expressed and purified (termed DE→A), where all of the aspartic acid and glutamic acid residues were substituted with alanine. Although the DE→A mutant exhibited a similar water uptake to wild type reflectin, PdHx devices from the DE→A mutant featured a current density of $0.9 (\pm 0.2)$ A/cm2 at 1.5 V across a set of 11 films, which was approximately an order of magnitude lower than that found for wild type reflectin (FIG. 2). This measurement provided convincing additional evidence for protonic conduction in bulk reflectin.

To further understand the conductive behavior of reflectin, the amino acid sequence of reflecting was dramatically altered. Reflectin's highly conserved primary sequence and multiple repeating domains are likely crucial for its quaternary structure, and by extension, its conductive behavior. Scrambling this sequence and eliminating the subdomains was expected to affect reflectin's ability to form extended hydrogen-bonded water networks, which facilitate Grotthuss-type proton transfer (See references 10,18). Therefore, a reflectin mutant (termed Random) was heterologously expressed and purified, where the amino acid order was scrambled, while the percentage of the individual amino acids (including the D and E residues) was maintained. Although the Random mutant exhibited a similar water uptake to wild type reflectin, PdHx devices from this variant featured a current density of $1.7 (\pm 0.3)$ A/cm2 at 1.5 V across a set of 11 films, which was approximately 5-fold lower than that measured for wild type reflectin. Interestingly, the current density of the Random mutant was 2-fold higher than the current density of the DE→A mutant, presumably due the Random mutant's higher proton-donating aspartic and glutamic amino acid content. Overall, the observations supported the notion that carboxylic acid containing residues serve as the proton source for reflectin and underscored the crucial importance of reflectin's primary sequence for its electrical properties.

To further characterize protonic conductivity in the films, they were interrogated by EIS as a function of temperature. Nyquist plots for reflectin devices contacted with blocking gold electrodes on glass over a temperature range of 30° C. to 65° C. were recorded; reflectin is expected to be stable across this range because it maintains its functionality even after processing at temperatures of 80° C. (See reference 46). By fitting the impedance data to the simple equivalent circuit, the bulk resistances of the reflectin films was extracted and these values were converted to conductivity (See references 56-60). Notably, at a relative humidity of 90% and a temperature of 65° C., a peak conductivity of $2.6\times10^{-3}$ S/cm was measured as was an average conductivity of $1.2 (\pm1)\times10^{-3}$ S/cm across a set of 3 films. These values compare favorably to the values found for other proton conducting materials and represent the state-of-the-art for any bulk solid-state material from a naturally occurring protein (See references 21-26).

Arrhenius-type conductivity plots were formulated from the temperature-dependent measurements, which allowed determination of the activation energy (Ea) of proton conduction for reflectin (See references 12, 52). This activation energy corresponds to the cost of dissociating and/or transporting protons through the hydrogen-bonded water networks presumably permeating the protein films (10, 20). The average value of Ea=0.21 ($\pm0.05$) eV calculated from a linear fit of the measurements was characteristic of a Grotthuss-type conduction mechanism (See references 10, 18-20). Similar activation energies have been found for proton conduction in gramicidin channels (Ea=~0.2 eV to ~0.3 eV) and dilute acids (Ea=~0.1 eV) (See references 10, 18-20). Given that electronic conduction would require activation energies corresponding to the high energetic cost of reducing/oxidizing amino acids (~1 V) (See references 53, 63, 64), the low observed activation energy provided additional confirmation of protonic conductivity for bulk reflectin.

Given that protonic conductors are important in a variety of high-technology applications, it was sought to demonstrate the utility of reflectin in a functional device. Protonic transistors were chosen because only a handful of these have been reported, none of which used a naturally occurring protein as the active material (See references 37-41). Three-terminal reflectin devices were fabricated featuring PdHx electrical contacts (formed in situ) on Si/SiO2 substrates; the PdHx contacts enabled the selective injection of protons into the film (See references 40,61).

The electrical properties of the reflectin-based transistors were studied. Protonic current between the source and drain (IDS) was recorded as a function of the applied potential between the source and drain (VDS), while modulating the gate bias (VGS). The measurements demonstrated electrostatic control over proton conduction: a negative VGS effectively induced the injection of protons into the channel, increasing the observed current, and a positive VGS depleted the channel of protons, decreasing the observed current. Notably, the electrostatic gating effects were remarkably reproducible, as exemplified by curves obtained from 4 typical devices. At low source-drain biases, a small barrier for current flow was found which was likely associated with the activation energy of proton dissociation/transport. Furthermore, in agreement with previous measurements, the IDS versus VDS curves exhibited hysteresis, presumably due to charge accumulation/depletion at the contacts (See reference 40). Negligible leakage currents were observed, as might be expected for a proton-conducting active material on a proton-insulating substrate. Overall, the findings demonstrated the excellent functionality of reflectin in protonic transistors.

As a consistency check, the conductivities calculated from the transistor measurements were compared with the values determined by EIS. The slope of the IDS versus VDS plot at VGS=0 V yielded an effective resistance for the reflectin films, which translated to a conductivity of $2.1 (\pm2.5)\times10^{-4}$ S/cm for six devices. This value was very similar to the conductivity of $1.0 (\pm0.5)\times10^{-4}$ S/cm found with electrochemical impedance spectroscopy at 25° C. Given the substantial experimental differences between the two techniques, the agreement is noteworthy, highlighting the robustness and reliability of the transistor measurements.

Finally, the proton mobility was extracted from the transistor measurements. The excess free protons in reflectin likely originate from deprotonation of reflectin's D and E amino acids, as suggested by the control experiments for the DE→A and Random mutants. By employing a literature protocol, the free proton concentration in the reflectin films was directly estimated as nH+=$2.2\times10^{17}$ cm-3 at VGS=0 V. Based on the equation H+=H+nH+e, the proton concentration and conductivity of $2.1\times10^{-4}$ S/cm yielded an effective proton mobility of $=5.4\times10^{-3}$ cm2 V-1 s-1, which was in excellent agreement with mobilities reported for proton conduction in dilute acid solutions (~$3\times10^{-3}$ cm2 V-1 s-1)20, PEDOT:PSS (~$3.9\times10^{-3}$ cm2 V-1 s-1)65, and maleic-chitosan proton conductors. Notably, these calculations, along with the measurements for the activation energy and conductivity of reflectin, indicate that this protein effectively exhibits the same electrical behavior as a dilute acidic solution.

Discussion

The reflectin protein was interrogated via humidity-dependent DC electrical measurements with both proton blocking and proton injecting contacts, AC electrical measurements in the presence of water and deuterated oxide, rationally guided mutagenesis experiments, and temperature-dependent electrochemical impedance spectroscopy studies. The findings indicate that reflectin functions as an efficacious proton conduction medium.

Based on the measurements, reflectin exhibits the characteristics of a dilute acid, with an average proton conductivity of $1.0\times10^{-4}$ S/cm, an activation energy of 0.21 eV, and a mobility of $5.4\times10^{-3}$ cm2 V-1 s-1. Bulk reflectin is quite unique in this regard; no other protein has been shown to so closely mimic a dilute acidic solution. Moreover, reflectin's maximum conductivity of $2.6\times10^{-3}$ S/cm at 65° C. represents the largest value discovered for any wild type protein. Within the context of other biological (and even artificial) proton-conducting materials, reflectin's figures of merit are impressive and effectively set new benchmarks for naturally occurring proteins in the solid state (See references 21-26).

Reflectin's excellent electrical properties enable the fabrication and characterization of the first protein-based protonic transistors. The transistor characteristics of reflectin-based devices are very similar to those previously reported for maleic chitosan-based devices in terms of mobility, threshold voltage, and on/off current ratio (See reference 40). However, relative to maleic chitosan, reflectin allows protonic transistors to leverage the distinct advantages of protein-based materials (See references 27-31). For example, the conductive properties of reflectin can be tuned via the rationally controlled, site-specific modulation of its amino acid sequence content and context. Consequently, given the few reported examples of protonic transistors and the possibilities available to functional protein-based materials, the devices represent a significant advance.

Here, it is important to note the excellent reproducibility of the measurements, as confirmed by the statistics quoted within the text. High quality, reproducible electrical measurements are known to be notoriously difficult for delicate protein-based systems, which can often undergo degradation (See references 6,10,36, 51-53). However, reflectin films readily withstand repeated electrical cycling, as evidenced by the electrochemical impedance studies and transistor measurements. These observations highlight not only to the reliability of the approach but also the overall robustness of reflectin as a protonic conductor. For a protein-based material, this rare combination of reproducibility and robustness represents a crucial and noteworthy advantage from the perspective of potential applications.

Finally, reflectin's function as a proton conducting material is especially fascinating if one takes into account the relatively low density of acidic amino acids and apparent lack of significant secondary/tertiary structure (See references 42-46). Interestingly, the tandem mutagenesis and electrical characterization studies, together with previous self-assembly experiments (See references 43,46) provide compelling evidence that reflectin may possess well-defined and potentially unique quaternary structural features in the solid state.

Example 2

Ionic transistors from organic and biological materials represent an emerging class of devices for bioelectronics applications. Indeed, the processing and fabrication techniques required for the preparation of these transistors are simple, convenient, and inexpensive. Moreover, the constituent organic or biological materials are amenable to chemical modification and functionalization. In addition, the mechanical properties of organic materials are inherently compatible with those of biological systems. Finally, organic and biological ionic conductors are well suited for the transduction of biochemical events into electronic signals. These key advantages have made ionic transistors from organic and biological materials exciting targets for further research and development.

Within the broader ionic transistor class of devices, there have been several reports of protonic transistors. For these devices, the application of a voltage to the gate modulates the current flow between the source and the drain, in analogy to conventional unipolar field effect transistors. The magnitude of the current is determined by the proton charge carrier density in the device channel, as given by Equation 1:

$$n_{H+} = n_{H+}^0 - V_{GS}C_{GS}/et \quad \text{Equation 1:}$$

where $n_{H+}$ is the proton concentration at an arbitrary gate voltage, $n_{H+}^0$ is the proton concentration at a gate bias of 0 V, $V_{GS}$ is the gate voltage, $C_{GS}$ is the gate capacitance, e is the charge of the proton, and t is the thickness of the active layer. Thus, a negative gate voltage induces the injection of protons into the channel, leading to an increase in the source-drain current, and a positive gate voltage depletes the channel of protons, leading to a decrease in the source-drain current. This operating mechanism enforces limits on the ratio between protonic transistors' high (on) and low (off) currents (IHIGH/ILOW), relative to standard field effect transistors.

However, the IHIGH/ILOW ratio, in principle, can be improved by reducing the active layer thickness, thereby increasing the difference between the transistors' high and low current states. As demonstrated in Example 1, reflectin, a structural protein that plays a key role in the color-changing abilities of cephalopods, is an effective proton conducting material. As described in Example 1, this finding enabled the fabrication of protein-based protonic transistors with excellent figures of merit, including a high proton mobility. However, due to active layers with thicknesses between 1 and 2 m, the transistors possessed relatively poor IHIGH/ILOW ratios of 1.6.

Herein, improved high/low current ratios for reflectin-based protonic transistors is demonstrated. Two-terminal devices were fabricated from thin reflectin films and their conductivity characterized when contacted with palladium (Pd) and palladium hydride (PdHx) electrodes. The electrical interrogation of reflectin films with an average thickness of 0.30 m was performed in a three-terminal transistor configuration. The majority of the device metrics, including mobility and proton concentration, are comparable to those previously reported for protonic transistors from reflectin films with a thickness between 1 and 2 m. However, a 2-fold improvement in the thin protonic transistors' high/low current ratios was observed. Overall, the findings highlight the importance of the active layer geometry for the performance of protein-based (and other) protonic transistors.

A histidine-tagged *Doryteuthis* (*Loligo*) *pealeii* reflectin A1 isoform was expressed in *E. coli* according to previously reported protocols. Crude reflectin was extracted from *E. coli* inclusion bodies. The protein was then sequentially purified by immobilized metal affinity chromatography under denaturing conditions and high performance liquid chromatography (HPLC). The identity of the purified protein was definitively confirmed by in-gel tryptic digestion and tandem mass spectrometry. Notably, the optimized expression and purification procedure yielded >800 mg of reflectin per liter of *E. coli* cell culture with a purity of over 99%. This high yield and excellent purity enabled the high throughput fabrication of reflectin-based devices.

For the measurements, two-terminal bottom-contact devices were fabricated In brief, an array of palladium contacts was deposited onto the surface of clean silicon dioxide/silicon (SiO2) substrates via electron-beam evaporation through a shadow mask. Next, aqueous reflectin solutions were dropcast onto the electrodes. The solvent was then allowed to evaporate, and the excess protein was removed from the substrate via mechanical scribing. The resulting completed devices were subjected to physical and electrical characterization.

Devices were characterized with both optical microscopy and atomic force microscopy (AFM). The film was uniform, with few apparent defects. The surface topography of the reflectin film is relatively smooth and featureless with a RMS of 0.4 nm. The devices were now poised for electrical characterization.

Electrical properties of the reflectin films were studied by recording current (I) as a function of voltage (V) at a relative humidity of 90%. The 0.24 m-thick device featured a low current density of 0.7→102 A/cm2 at 1.5 V, consistent with previous findings for 1 to 2 m-thick reflectin films contacted with proton-blocking electrodes. Subsequently, the device's electron-conducting Pd contacts were converted into proton-injecting PdHx contacts via exposure to hydrogen gas in situ. The current density of the device increased by nearly an order of magnitude to 5.9 A/cm2 at 1.5 V, in agreement with literature precedent. These measurements confirmed the presence of protonic conductivity for thin reflectin films.

The electrical properties of reflectin films featuring an average thickness of 0.30 (±0.06) m were studied in a three-terminal transistor configuration The protonic source-drain current (ISD) in these devices, measured at different source-drain voltages (VSD), was dictated by the applied gate voltage (VGS). The protonic current decreased upon changing the VGS from +10 V to 0 V to 10 V at a relative humidity of 90%. This gating behavior was consistent with previous studies of maleic-chitosan-based and the reflectin-based protonic transistors described in Example 1. Proton mobility was calculated from the I-V characteristics of the transistors from thin reflectin films via established literature protocols. Conductivity from the transistors' ISD vs. VSD curves was extracted and used in a linear fit of the dependence of this conductivity on VGS to calculate the corresponding proton mobilities. The average calculated value of H+ was $7.7 \cdot 10^{-3}$ cm$^2$ V$^{-1}$s$^{-1}$ and the average charge carrier density ($n_{H+}$) of $2.5 \times 10^{17}$ cm$^{-3}$ for thin reflectin films and was similar to the previously reported values in thicker 1 to 2 m films, PEDOT:PSS films, and maleic chitosan nanofibers.

The proton charge carrier density of the thin reflectin films was determined according to established procedures. For example, at a VGS=0 V, an average charge carrier density ($n_{H+}$) of $2.5 \times 10^{17}$ cm$^{-3}$ was observed. This value was similar to that previously reported for both thick reflectin films and other proton-conducting materials. The charge carrier density of the films at different values of VGS was evaluated.

Notably, the experimentally determined charge carrier density was in excellent agreement with the one theoretically predicted by Equation 1. Finally, the IHIGH/ILOW ratios of protonic transistors from thin reflectin films was calculated. A ratio of 3.3 (±0.3) between the high current state at VGS=10 V and the low current state at VGS=+10 V was measured. This IHIGH/ILOW ratio of 3.3 represented a 2-fold improvement over the value of 1.6 previously found for thick reflectin films in Example 1. Although this ratio was certainly below values of >106 reported for organic transistors, it compared favorably to the best values found for protonic transistors under comparable conditions and in analogous configurations. These observations underscored the excellent performance of the thin reflectin film-based protonic transistors. Transistors from thin reflectin films feature a more than 2-fold improvement in their IHIGH/ILOW ratio relative to transistors from thick reflectin films.

The ratio of 3.3 compares favorably to the best values reported for similar devices. In their totality, our findings highlight the importance of the active layer geometry for optimum protonic transistor functionality.

All patents, patent applications, and publications cited in this specification are herein incorporated by reference to the same extent as if each independent patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

REFERENCES CITED

1. Caldin, E. F., Gold, V., eds. *Proton-transfer Reactions*, (Chapman and Hall, London, 1975).
2. Müller, A., Ratajczak, H., Junge, W., Diemann, E., eds. *Electron and Proton Transfer in Chemistry and Biology: Studies in Physical and Theoretical Chemistry*, vol. 78 (Elsevier, Amsterdam, 1992).
3. Karlin, K. D., Kramarz, K. W., Norton, J. R. *Slow Proton-Transfer Reactions in Organometallic and Bioinorganic Chemistry* (Wiley, New York, 1994).
4. Douhal, A., Lahmani, F., Zewail, A. H. Proton-transfer reaction dynamics. *Chem. Phys.* 207, 477-498 (1996).
5. Weinberg, D. R. et al. Proton-coupled electron transfer. *Chem. Rev.* 112, 4066-4093 (2012).
6. Schulten, Z., Schulten, K. Proton conduction through proteins: an overview of theoretical principles and applications. *Methods Enzymol.* 127, 419-438 (1986).
7. DeCoursey, T. E. Voltage-gated proton channels and other proton transfer pathways. *Physiol. Rev.* 83, 475-579 (2003).
8. DeCoursey, T. E. Voltage-gated proton channels: what's next? *J. Physiol.* 586, 5305-5324 (2008).
9. Gensch, T., Heberle, J., Viappiani, C. Proton transfer in biological systems. *Photochem. Photobiol.* 5, 529-530 (2006).
10. Wraight, C. A. Chance and design—proton transfer in water, channels, and bioenergetics processes. *Biochim. Biophys. Acta.* 1757, 886-912 (2006).
11. Colomban, P., ed. *Proton Conductors: Solids, Membranes and Gels—Materials and Devices* (Cambridge Univ. Press, Great Britain, 1992).
12. Kreuer, K. Proton conductivity: materials and applications. *Chem. Mater.* 8, 610-641 (1996).
13. Kreuer, K., Paddison, S. J., Spohr, R., Schuster, M. Transport in proton conductors for fuel-cell applications: stimulations, elementary reactions, and phenomenology. *Chem. Rev.* 104, 4637-4678 (2004).
14. Mauritz, K. A., Moore, R. B. State of understanding of nafion. *Chem. Rev.* 104, 4535-4385 (2004).
15. Norby, T. Proton conduction in solids: bulk and interfaces. *MRS Bull.* 34, 923-928 (2009).
16. Fabbri, E., Pergolesi, D., Traversa, E. Materials challenges toward proton-conducting oxide fuel cells: a critical review. *Chem. Soc. Rev.* 39, 4355-4369 (2010).
17. Yoon, M., Suh, K., Natarajan, S., Kim, K. Proton Conduction in metal-organic frameworks and related modularly built porous solids. *Angew. Chem. Int. Ed.* 52, 2688-2700 (2013).
18. Grotthuss, C. J. T. de. "Sur la décomposition de l'eau et des corps qu'elle tient en dissolution à l'aide de l'électricité galvanique". *Ann. Chim.* 58, 54-73. (1806).
19. Agmon, N. The Grotthuss mechanism. *Chem. Phys. Lett.* 244, 456-462(1995).
20. Cukierman, S. Et to Grotthuss! and other unfinished stories. *Biochim. Biophys. Acta.* 1757, 876-885 (2006).
21. Algie, J. E., Downes, J. G., Mackay, B. H. Electrical conduction in keratin. *Text. Res. J.* 30, 432-434 (1960).
22. Bardelmeyer, G. H. Electrical conductivity in hydrated collagen. I. Conductivity mechanisms. *Biopolymers* 12, 2289-2302 (1973). 23. Murphy, E. J. Ionic conduction in Keratin (wool). *J. Colloid Interface Sci.* 54, 400-408 (1976).
24. Tredgold, R. H. Sproule, R. C., McCanny, J. Proton conduction in protein films. *J. Chem. Soc., Faraday Trans.* 1 72, 509-512 (1976).
25. Careri, G., Geraci, M., Giasanti, A., Rupley, J. A. Protonic conductivity of hydrated lysozyme powders at megahertz frequencies. *Proc. Natl. Acad. Sci. USA* 82, 5342-5346 (1985).

26. Gabriel, B., Teissie, J. Proton long-range migration along protein monolayers and its consequence on membrane coupling. *Proc. Natl. Acad. Sci. USA* 93, 14521-14525 (1996).
27. Kaplan, D., McGrath, K., eds. *Protein-Based Materials—Bioengineering of Materials* (Birkhäuser, Massachusetts, 1996).
28. Maskarinec, S. A., Tirrell, D. A. Protein engineering approaches to biomaterials design. *Curr. Opin. Biotechnol.* 16, 422-426 (2005).
29. Shen, L., Bao, N., Zhou, Z., Prevelige, P. E., Gupta, A. Materials design using genetically engineered proteins. *J. Mater. Chem.* 21, 18868-18876 (2011).
30. DiMarco, R. L., Heilshorn, S. C. Multifunctional materials through modular protein engineering. *Adv. Mater.* 24, 3923-3940 (2012).
31. Grove, T. Z., Regan, L. New materials from proteins and peptides. *Curr. Opin. Struct. Biol.* 22, 451-456 (2012).
32. Owens, R. M., Malliaras, G. G. Organic electronics at the interface with biology. *MRS Bull.* 35, 449-456 (2010).
33. Svennersten, K., Larsson, K. C., Berggren, M., Richter-Dahlfors, A. Organic bioelectronics in nanomedicine. *Biochim. Biophys. Acta* 1810, 276-285 (2011).
34. Tarabella, G. et. al. New opportunities for organic electronics and bioelectronics: ions in action. *Chem. Sci.* 4, 1395-1409 (2013).
35. Glowacki, E. D., Irimia-Vladu, M., Bauer, S., Sariciftci, N. S. Hydrogen-bonds in molecular solids—from biological systems to organic electronics. *J. Mater. Chem. B* 1, 3742-3753 (2013).
36. Meredith, P., Bettinger, C. J., Irimia-Vladu, M., Mostert, A. B., Schwenn, P. E. Electronic and optoelectronic materials and devices inspired by nature. *Rep. Prog. Phys.* 76, 034501-034537 (2013).
37. Petrenko, V. F., Maeno, N. Ice field transistors. *J. Phys.* 148, 115-119 (March 1987).
38. Chiragwandi, Z. G., Nur, O., Willander, M., Calander, N. dc characteristics of a nanoscale water-based transistor *Appl. Phys. Lett.* 83, 5310-5312 (2003).
39. Fan, R., Huh, S., Yan, R., Arnold, J., Yang, P. Gated proton transport in aligned mesoporous silica films. *Nat. Mater.* 7, 303-307 (2008).
40. Zhong, C. et al. A polysaccharide bioprotonic field-effect transistor. *Nat. Commun.* 2, (2011) doi:10.1038/ncomms1489.
41. Dem, A. M., Bunge, A. L., Reznikov, M. A., Kolessov, A., O'Hayrel, R. P. Progress toward a solid-state ionic field effect transistor. *J. Appl. Phys.* 111, 074511-074518 (2012).
42. Crookes, W. J. et al. Reflectins: the unusual proteins of squid reflective tissues. *Science* 303, 235-238 (2004).
43. Kramer, R. M., Crookes-Goodson, W. J., Naik, R. R. The self-organizing properties of squid reflectin protein. *Nat. Mater.* 6, 533-538 (2007).
44. Tao, A. R. et al. The role of protein in assembly in dynamically tunable bio-optical tissues. *Biomaterials* 31, 793-801 (2010).
45. Izumi, M. et al. Changes in reflectin protein phosphorylation are associated with dynamic iridescence in squid. *J. R. Soc. Interface* 7, 549-560 (2010). 17
46. Phan, L. et al. Reconfigurable infrared camouflage coatings from a cephalopod protein. *Adv. Mater.* doi: 10.1002/adma.201301472
47. Mäthger, L. M., Denton, E. J., Marshall, N. J., Hanlon, R. T. Mechanisms and behavioural functions of structural coloration in cephalopods. *J. R. Soc. Interface* 6, 149-163 (2009).
48. DeMartini, D. G., Krogstad, D. V., Morse, D. E. Membrane invaginations facilitate reversible water flux driving tunable iridescence in a dynamic biophotonic system. *Proc. Natl. Acad. Sci. USA* 110, 2552-2556 (2013).
49. Wardill, T. J., Gonzalez-Bellido, P. T., Crook, R. J., Hanlon, R. T. Neural control of tunable skin iridescence in squid. *Proc. R. Soc. London Ser. B* 279, 4243-4252 (2012).
50. Ursúa, A., Gandía, L. M., Sanchis, P. Hydrogen Production from Water Electrolysis: Current Status and Future Trends. *Proc. IEEE* 410-426 (2012).
51. Zeng, K., Zhang, D. Recent progress in alkaline water electrolysis for hydrogen production and applications. *Progr. Energ. Combustion Sci.* 36, 307-326 (2010).
52. Glasser, L. Proton conduction and injection in solids. *Chem. Rev.* 75, 21-65 (1975).
53. Cordes, M., Giese, B. Electron transfer in peptides and proteins. *Chem. Soc. Rev.* 38, 892-901 (2009).
54. Shinwari, W., Deen, J., Starikov, E., Cuniberti, G. Electrical conductance in biological molecules. *Adv. Funct. Mater.* 20, 1865-1883 (2010).
55. Ron, I., Pecht, I., Sheves, M., Cahen, D. Proteins as solid-state electronic conductors. *Acc. Chem. Res.* 43, 945-953 (2010).
56. Barsukov, E., Macdonald, J. R., eds. *Impedance Spectroscopy: Theory, Experiment and Applications,* 2nd ed. (Wiley, New Jersey, 2005).
57. Yuan, X., Song, C., Wang, H., Zhang, J. *Electrochemical Impedance Spectroscopy in PEM Fuel Cells: Fundamentals and Applications* (Springer-Verlag, London, 2012).
58. Huggins, R. A. Simple method to determine electronic and ionic components of the conductivity in mixed conductors: a review. *Ionics* 8, 300-313 (2002).
59. Xie, Z. et al. Discrepancies in the measurement of ionic conductivity of PEMs using two- and four-probe AC impedance spectroscopy. *J. Electrochem. Soc.* 153, 173-178 (2006).
60. Soboleva, T. et al. Investigation of the through-plane impedance technique for evaluation of anisotropy of proton conducting polymer membranes. *J. Electroanal. Chem.* 622, 145-152 (2008).
61. Morgan, H., Pethig, R., Stevens, G. T. A proton-injecting technique for the measurement of hydration-dependent protonic conductivity. *J. Phys. E. Sci. Instrum.* 19, 80-82 (1986).
62. Creighton, T. E. *Proteins: Structures and Molecular Properties,* 2nd ed. (W. H. Freeman & Co., New York, 1993).
63. Malfoy, B., Renaud, J. A. Electrochemical investigations of amino acids at solid electrodes: part I. sulfur components: cystine, cysteine, methionine. *J. Electroanal. Chem.* 114, 195-211 (1980).
64. Malfoy, B., Renaud, J. A. Electrochemical investigations of amino acids at solid electrodes: part II. amino acids containing no sulfur atoms: tryptophan, tyrosine, histidine, and derivatives. *J. Electroanal. Chem.* 114, 213-223 (1980).
65. Stavrinidou, E., Leleux, P., Rajaona, H., Khodagholy, D., Rivnay, J., Lindau, M., Sanaur, S., Malliaras, G. G. Direct measurement of ion mobility in a conducting polymer. *Adv. Mater.* 25, 4488-4493 (2013).

What is claimed is:

1. A method of conducting protons from a proton source to a proton sink, comprising
conducting protons through a protonic channel structure comprising a cephalopod proton-conducting protein, wherein the cephalopod proton-conducting protein comprises
a protein comprising SEQ ID NO: 1, and/or
a reflectin.

2. The method of claim 1, wherein
the cephalopod proton-conducting protein is a reflectin.

3. The method of claim 1, wherein
the channel structure comprises a thin film of cephalopod proton-conducting protein.

4. The method of claim 1, wherein
the protonic channel structure comprises a composite material comprising cephalopod proton-conducting protein coated particles embedded in a matrix.

5. The method of claim 1, wherein
the proton source and proton sink comprise electrodes, wherein a differential voltage exists between the two electrodes.

6. The method of claim 5, wherein
the electrodes comprise metal hydride electrodes.

7. The method of claim 1, wherein
the proton source and proton sink comprise separate compartments in a device selected from the group consisting of:
an electrochemical cell, a fuel cell, an electrolyzer, and a battery.

8. The method of claim 1, wherein the protonic channel structure comprises a cephalopod proton-conducting protein-coated mesh or porous material.

9. The method of claim 1, wherein
the proton sink comprises a biological system.

10. The method of claim 9, wherein
the biological system is selected from a group consisting of:
an intracellular space, an extracellular space, a tissue, and a cell culture.

11. The method of claim 1, further comprising
the modulation of the protonic channel structure's protonic conductivity by the application of an electric field to the channel structure.

12. The method of claim 11, wherein the electric field is applied by a gate electrode in contact with or in proximity to the channel structure.

\* \* \* \* \*

SEQUENCE LISTING

<160> NUMBER OF SEQ ID NOS: 1

<210> SEQ ID NO 1
<211> LENGTH: 27
<212> TYPE: PRT
<213> ORGANISM: Doryteuthis pealeii
<220> FEATURE:
<221> NAME/KEY: MISC_FEATURE
<222> LOCATION: (1)..(1)
<223> OTHER INFORMATION: The first residue may be either methionine or
      phenylalanine
<220> FEATURE:
<221> NAME/KEY: MISC_FEATURE
<222> LOCATION: (3)..(7)
<223> OTHER INFORMATION: Xaa can be any naturally occurring amino acid
<220> FEATURE:
<221> NAME/KEY: MISC_FEATURE
<222> LOCATION: (8)..(14)
<223> OTHER INFORMATION: The motif comprising residues 8-14  may be
      omitted
<220> FEATURE:
<221> NAME/KEY: MISC_FEATURE
<222> LOCATION: (10)..(14)
<223> OTHER INFORMATION: Xaa can be any naturally occurring amino acid
<220> FEATURE:
<221> NAME/KEY: MISC_FEATURE
<222> LOCATION: (15)..(21)
<223> OTHER INFORMATION: The motif comprising residues 15-21  may be
      omitted
<220> FEATURE:
<221> NAME/KEY: MISC_FEATURE
<222> LOCATION: (17)..(21)
<223> OTHER INFORMATION: Xaa can be any naturally occurring amino acid
<220> FEATURE:
<221> NAME/KEY: MISC_FEATURE
<222> LOCATION: (24)..(27)
<223> OTHER INFORMATION: Xaa can be any naturally occurring amino acid
<220> FEATURE:
<221> NAME/KEY: MISC_FEATURE
<222> LOCATION: (27)..(27)
<223> OTHER INFORMATION: Residue 27 may be omitted

<400> SEQUENCE: 1

Met Asp Xaa Xaa Xaa Xaa Xaa Met Asp Xaa Xaa Xaa Xaa Xaa Met Asp
1               5                   10                  15

Xaa Xaa Xaa Xaa Xaa Met Asp Xaa Xaa Xaa Xaa
            20                  25